US010285304B1

(12) United States Patent
Lin

(10) Patent No.: US 10,285,304 B1
(45) Date of Patent: May 7, 2019

(54) RACK-LEVEL TEST ROOM

(71) Applicant: ZT Group Int'l, Inc., Secaucus, NJ (US)

(72) Inventor: Ting Yu Lin, Bloomfield, NJ (US)

(73) Assignee: ZT Group Int'l, Inc., Secaucus, NJ (US)

( * ) Notice: Subject to any disclaimer, the term of this patent is extended or adjusted under 35 U.S.C. 154(b) by 161 days.

(21) Appl. No.: 15/223,168

(22) Filed: Jul. 29, 2016

(51) Int. Cl.
*H05K 7/20* (2006.01)
*G01N 19/10* (2006.01)
*G01F 1/76* (2006.01)
*G01K 7/02* (2006.01)

(52) U.S. Cl.
CPC ........... *H05K 7/20136* (2013.01); *G01F 1/76* (2013.01); *G01K 7/02* (2013.01); *G01N 19/10* (2013.01); *H05K 7/20145* (2013.01)

(58) Field of Classification Search
CPC .... H05K 7/20145; H05K 7/1485; H05K 7/20; H05K 7/20009; H05K 7/20836; G01N 19/10; G01F 1/76; G01K 7/02
USPC ...................... 73/865.6, 865.8; 374/142, 210; 165/11.1, 11.2, 47–57, 67, 108, 132, 138, 165/157, 159–162, 168–171; 236/1, 1 R, 236/1 C, 44 R, 44, 91 E, 93 R, 97; 137/597, 599.01–599.07, 602, 896, 897, 137/605, 606, 861, 883; 454/188, 193, 454/234, 237, 241, 256, 184
See application file for complete search history.

(56) References Cited

U.S. PATENT DOCUMENTS

| | | | |
|---|---|---|---|
| 7,363,831 B2 | 4/2008 | Willemin | |
| 2011/0195652 A1* | 8/2011 | Smith | H05K 7/20836 454/184 |
| 2012/0009862 A1 | 1/2012 | Meyer | |

* cited by examiner

*Primary Examiner* — Robert R Raevis
(74) *Attorney, Agent, or Firm* — Dergosits & Noah LLP; Todd A. Noah

(57) ABSTRACT

A rack test room is disclosed that provides a controlled and monitored environment for one or more server racks, the room controlling and monitoring the cold aisle temperature, the cold aisle air inlet flow rate, and the hot aisle temperature. A rack test room is disclosed that monitors the inlet and exhaust air temperatures for each server in a rack. A rack test room is disclosed that individually controls and monitors the inlet air flow rate to each of a plurality of server racks. A method is disclosed for using a rack test room to simulate a data center environment.

14 Claims, 6 Drawing Sheets

RACK-LEVEL TEST ROOM

BACKGROUND

Walk-in thermal chambers may be used in the industry for rack-level thermal testing. Such chambers may allow testing at uniform temperature and humidity. However, typical thermal chambers are not equipped to maintain hot and cold aisles that a separated by the racks and servers being tested. Furthermore, typical thermal chambers are not equipped to control and monitor cold aisle air inlet temperatures and inlet air flow rates. Examples of typical chambers include Modular Walk-In Chambers, Welded Walk-In Chambers, and Stability Walk-In Rooms supplied by CSZ Industrial of Cincinnati, Ohio.

But in a data center environment, a server rack is positioned between a hot aisle and a cold aisle to achieve a higher cooling efficiency. In the typical configuration, the ambient or cold air temperature aisle is at the front of the rack and the hot aisle is at the back. The air temperature between the cold and hot aisles may show a gradient between the two and be considered a "warm" zone.

Thus, it is apparent that typical thermal chambers are not equipped to simulate the conditions under which a server rack may be used, or provide detailed information regarding individual servers in a server rack.

Without such information from a rack-level test room it is difficult to assess the effects of hardware design changes (server, rack, or room) on thermal performance, or on the thermal performance of other elements in the system. For example, by not monitoring and controlling air flow rates and temperatures typical thermal chambers cannot test the effect of those data center variable on server or rack performance.

Therefore, the need exists for a solution that allows both the control and monitoring of many elements of the environment of a rack test room.

DETAILED DESCRIPTION

Figure 1:
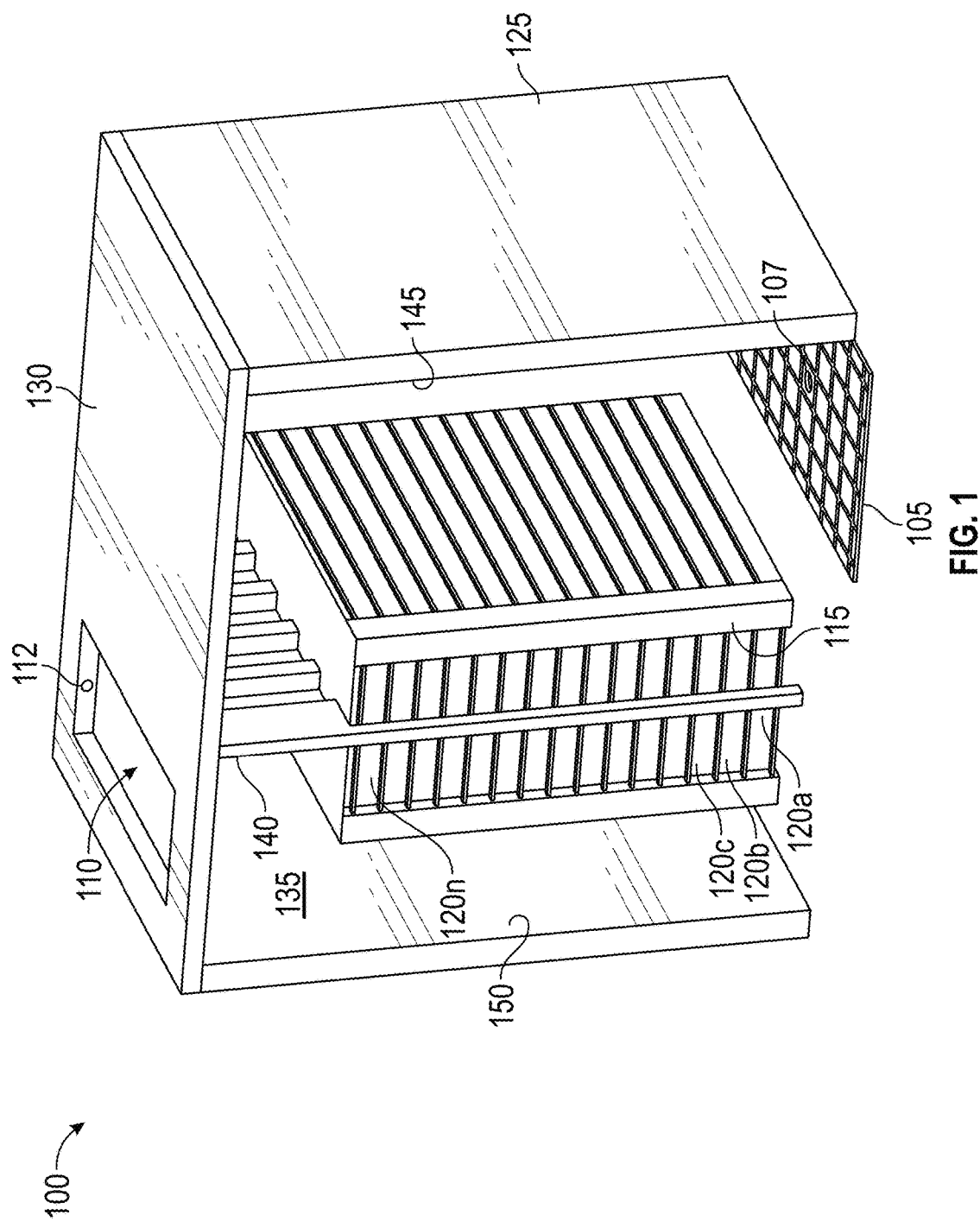
FIG. 1 is a perspective drawing illustrating an embodiment of a rack test room.

In an embodiment, a rack test room simulates the environment of a data center on a smaller scale and provides the ability to vary environmental parameters to test a parameter's effect on the performance of a rack and associated servers, and to test the performance of the data center. A parametric study of different environmental parameters (e.g., air flow rate, temperature, and humidity) using an embodiment of a rack test room may assist in optimizing a hardware design, e.g., rack design, server design, or data center design. Being able to test such parameters at the rack and server level may improve testing efficiency with the result that improvements to the rack, server, or data center may be recognized and implemented sooner.

In an embodiment, a rack test room may generate an environment that is similar to the environment of a data center. In an embodiment, the rack test room is able to monitor and control its environmental parameters to allow the controlled thermal testing of rack and server combinations. Such testing may provide useful information revealing (or verifying) issues that the tested rack and server combination may experience if installed in a particular data center. In response, solutions may be proposed and tested before an actual problem is experienced in the data center.

In an embodiment, a rack test room is instrumented with sensors that may provide detailed information, such as temperature data (e.g., inlet air temperature, hot and cold aisle temperatures, individual server inlet and exhaust air temperatures) and air flow rate data (e.g., inlet air flow rate from a single source or each of multiple sources). Such data may be used in determining, for example, the thermal performance of servers at different inlet air flow rates or temperatures, or the amount of air recirculation from hot aisle to cold aisle. Furthermore, the environment of the rack test room may be controlled by, for example: controlling an air-conditioning system so that it provides supply air of a desired temperature and a desired humidity; controlling a supply fan (or blower) so that it provides supply air at a desired flow rate; and controlling flow control valve so that air is supplied to the test room from a desired inlet and at a desired flow rate. Additionally, the rack and servers within the test room may be instrumented to determine rack or server-specific data, e.g., inlet and exhaust air temperatures for each server. All such data, i.e., temperature data, air flow rate data, humidity data, and control signals to the fans, valves, and air conditioning system, may be recorded by a data acquisition system.

In an embodiment, a rack test room may house a number of racks. In such racks, the servers are typically oriented so that the fronts of the servers face a cold aisle. Heat generated by the server operation is then exhausted from the back of the server, which creates a hot aisle. The cold aisle thus separated by the rack and servers. In an embodiment, the separation between the hot and cold aisles is enhanced by placing a membrane such as a curtain between the rack/server sides and corresponding walls and between the rack top and ceiling. In an embodiment, one or more fans (e.g., DC fans) may be directed at the top of a rack, at the bottom of a rack, or at both top and bottom, or at any desired rack location, to supply cooling air. In an embodiment, the fan speed may be adjustable to control the supply air flow rate to the rack at which a particular fan is directed.

Thus, an embodiment may provide the following benefits: an environment with hot aisle and cold aisle containment similar to that of a data center; cooling air available from a lower source, from an upper source, or from some combination of sources; inlet air flow rate control; supply air temperature control; and supply air humidity control.

In an embodiment, the rack test room may be a portable room, chamber, or other type of housing or enclosure.

An embodiment directed to a test room for multiple racks may provide the ability to individually control the air flow to each of the racks.

Based on data provided by an embodiment, an overall system (e.g., the combination of a data center and its server racks) may be controlled to increase or decrease the amount of cooling, which may improve the system's energy efficiency, or the servers' performance, or both.

FIG. 1 is a perspective drawing illustrating an embodiment of a rack test room 100. In FIG. 1, test room 100 may provide rack 115 with a controlled environment. Test room 100 therefore contains rack 115 with walls 125, 135, ceiling 130, a floor, and two additional walls that are not shown so that elements of test room 100 may be shown more clearly. An entrance, also not shown for clarity, provides access to test room 100. Test room 100 is equipped with an air inlet 105 in the floor and an air exhaust 110 in ceiling 130. Air inlet 105 is for providing conditioned air to test room 100 and air exhaust 110 is for allowing air to leave test room 100. Air inlet 105 may receive conditioned air through ducting from an air-conditioning system, not shown, that provides air inlet 105 with air of a controlled temperature and of a controlled humidity. Air exhaust 110 may be connected to ducting that may direct exhaust air to a desired external location or to an inlet for the air-conditioning system. Air inlet 105 is provided with a thermocouple 107 for measuring the incoming air temperature. Air exhaust 110 is provided with a thermocouple 112 for measuring the exhaust air temperature. Thermocouples 107 and 112 may be connected to a data acquisition system, not shown, or other apparatus to facilitate the recording of test conditions. Thermocouples 107 and 112 may be connected to simple readouts with test conditions being recorded manually. One of skill will realize that there are many ways to record the data from such tests.

In FIG. 1, rack 115 is filled with servers, e.g., servers 120a, 120b, 120c, . . . 120n, which create heat when used. A server typically draws in cooling air from the front end and exhausts heated air from the back. Servers 120a, b, c, . . . n, are typically oriented in the same way within rack 115. Thus, in rack 115, all servers draw cooling air from the front end and exhaust heated air out the back. In the embodiment, cooled air from air inlet 105 creates a cold aisle 145. The servers in rack 115 draw cooling air from cold aisle 145 and exhaust heated air, creating a hot aisle 150. Air from hot aisle 150 escapes test room 100 through air exhaust 110 and may then be ducted to an external location or to the inlet of the air conditioning system. In an embodiment, the air from air inlet 105 is also humidity controlled.

In an embodiment, a membrane 140, such as a drape, may be placed about rack 115 between cold aisle 145 and hot aisle 150 to inhibit the movement of air around or over rack 115. The use of membrane 140 may be advised where it is desired to simulate an environment in which rack 115 is sandwiched between other racks.

In an embodiment, test room 100 may be dimensioned to accommodate two or more racks similar to rack 115 for testing. In an embodiment, the open areas of air inlet 105 and air exhaust 110 may be adaptable so that they may be changed in proportion to the number of racks being tested. For example, should two racks be tested, air inlet 105 might be made twice as long as air inlet 105 would be if only one rack were being tested. The same may hold for air exhaust 110. Such adaptability may allow data center conditions to be simulated more realistically.

Figure 2:
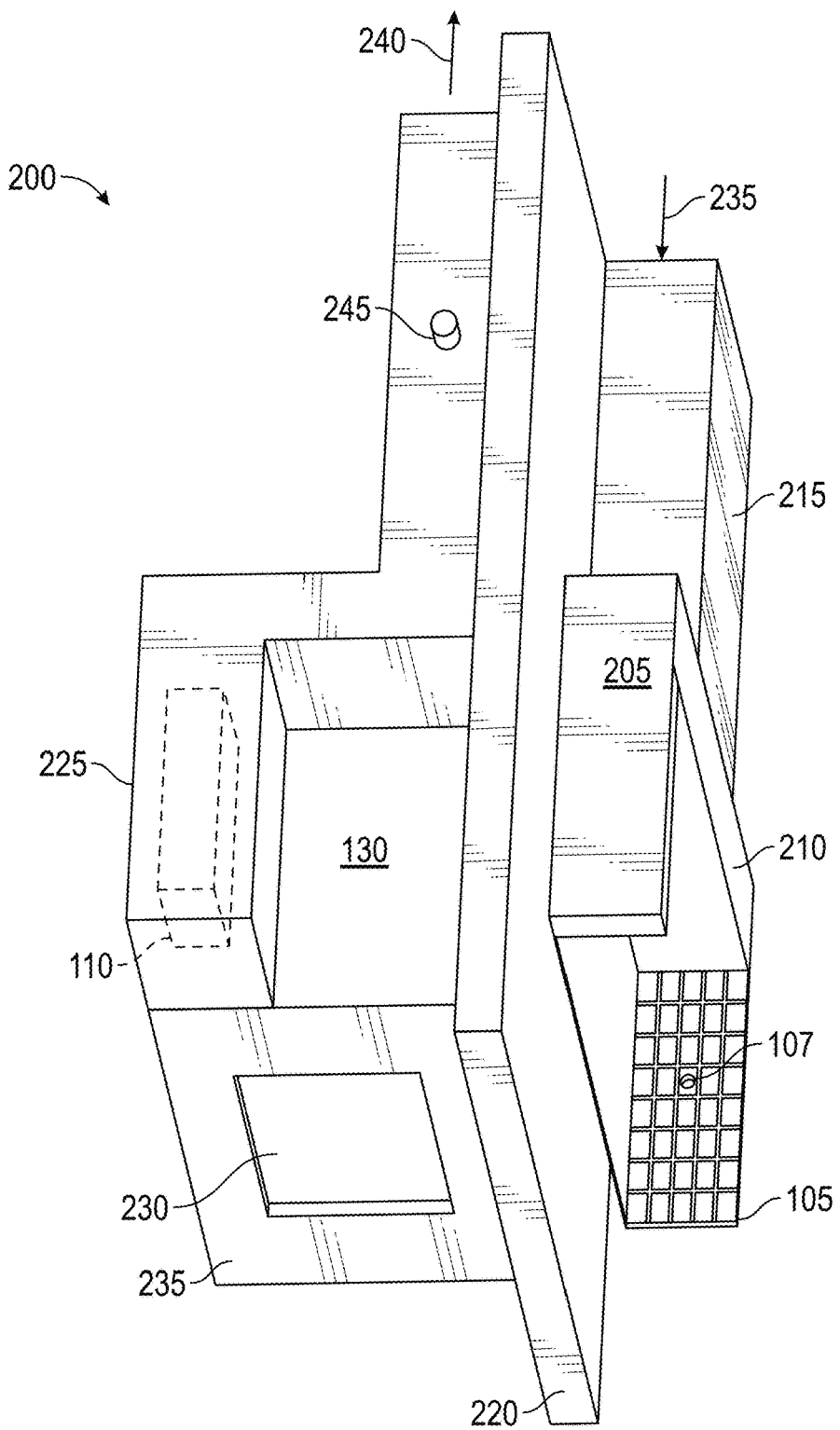
FIG. 2 is a perspective drawing illustrating an embodiment of a rack test room.
Figure 3:
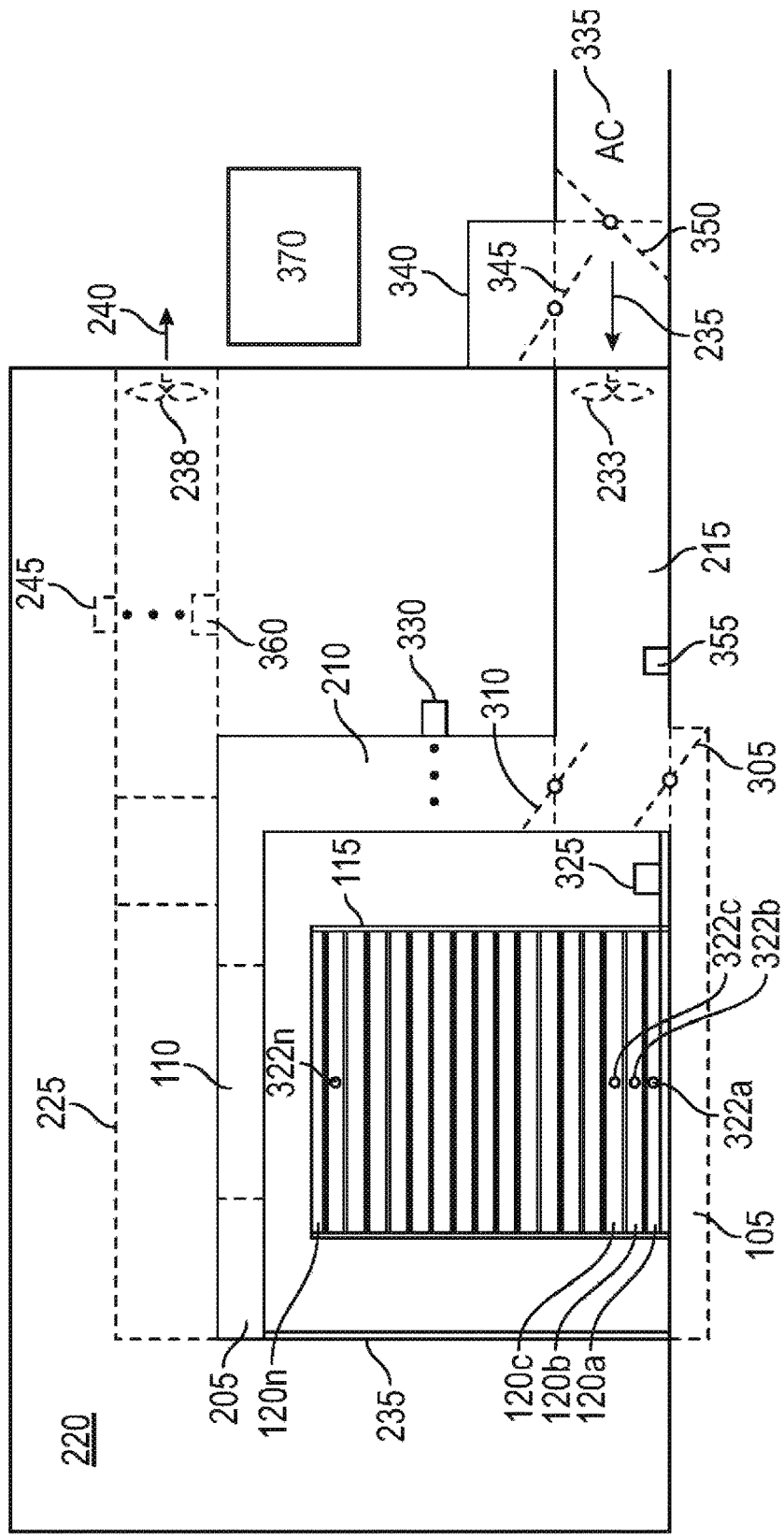
FIG. 3 is a side view drawing illustrating an embodiment of a rack test room.

FIG. 2 is a perspective drawing illustrating an embodiment of a rack test room 200. In FIG. 2, rack test room 200 has a support structure 220 and an upper air inlet 205 (seen from above). Upper air inlet 205 and lower air inlet 105 are connected by a duct 210 to a supply duct 215, which receives a conditioned supply air 235 from an air-conditioning system 335 (FIG. 3). A wall is not shown on the right side of test room 200 and a part of a wall 235 is not shown on the front of test room 200 so that air inlets 105, 205 may be viewed more clearly. Test room 200 includes a window 230 in wall 235 and an exhaust duct 225 for receiving air from exhaust 110 and directing it externally as exhaust air 240. In an embodiment, exhaust air 240 is directed to an air-conditioning system that supplies inlet air 235. An air flow meter 245 measures the flow of exhaust air. Similar air-flow meters 325, 330 (FIG. 3) measure the flow of air to lower air inlet 105 and upper air inlet 205. One of skill will realize that when test room 200 is closed the mass air flow in must be substantially equal to the mass air flow out. For this reason, two air flow measuring devices would suffice to determine the flow through each of the three ducts (2 air inlets and 1 exhaust). Air flow meter 245 may be, for example, a paddle-wheel measuring device or a measuring device based on the Venturi principle. In the embodiment, the lower air inlet 105 and the upper air inlet 205 provide the option for conditioned air to be supplied from below, from above, or from both simultaneously. Thus, in an embodiment, two flow control valves 310, 305 (FIG. 3) are fitted within duct 210 so that air inlet 105 and air inlet 205 may be controlled independently. In an embodiment, fans (or blowers) 233 and 238 may work with an air conditioning system or work without an air conditioning system to circulate air through test room 200. In an embodiment, an air conditioning system, by itself causes air to circulate through test room 200.

In FIG. 2, cooling air supplied from lower air inlet 105, upper air inlet 205, or both, represents the total cooling air supplied to test room 200. Test room 200 may house multiple racks, such as rack 115. In the embodiment, supply fans 233, or 238, or both are controlled to supply cooling air. Based on the data collected through sensors (thermocouples, flow meters, humidity sensors, and other internal sensors) supply fans 233 and 238 may be controlled to dynamically vary the cooling provided. Such real-time data measurement and evaluation, and control of the air supply temperature, or flow, or both, based on that evaluation can improve the performance of servers on racks within test room 200 by dynamically adapting the environment of test room 200 to improve server thermal performance.

FIG. 3 is a right side view drawing further illustrating the embodiment of rack test room 200 of FIG. 2. In FIG. 3, wall 125 (FIG. 2) has been made transparent for clarity. In FIG. 3, each server 120a, 120b, 120c, . . . ,120n, in rack 115 may be fitted with a corresponding server inlet air temperature sensor 322a, 322b, 322c, . . . , 322n. The server inlet air temperature sensors may be, e.g., thermocouples. Similarly, each server may be equipped with a corresponding server exhaust air temperature sensor, not shown, on the opposing side of each server. An air conditioning system 335 may provide supply air 235. Supply air 235 is preferably but not necessarily temperature and humidity controlled. That is, supply air 235 may be provided simply by fan 235 from an external source 340. The flow of supply air 235 into test room 200 may be controlled by flow control valves 305, 310. The source of supply air 235 may be controlled by flow control valves 345 and 350. Flow control valves 305, 310, 345, and 350 may be, for example, controllable dampers. Flow control valves 305 and 310 may be individually controlled so that air may be provided to test room 200 by lower air inlet 105 and upper air inlet 205 at the same time, or from either of the two. Similarly, flow control valves 345, 350 may be independently controlled, though preferably, if air conditioning system 335 is selected as the source of supply air 235, flow control valve 345 is closed. In an embodiment, exhaust air 240 may be ducted (not shown) to an inlet for air conditioning system 335 to create a recirculating system. Duct 210 has been equipped with an air flow meter 330 for measuring the flow to upper air inlet 205. An air flow meter 325 has been positioned between duct 210 and lower air inlet 105 to measure the flow of air to air inlet 105. In an embodiment, a humidity sensor 335 may be positioned somewhere within the flow of supply air 235, for example, within duct 215. Similarly, a humidity sensor 360 may be positioned within the flow of exhaust air 240.

In an embodiment, data from the various measuring devices and controlled devices may be collected by a data acquisition system 370. For example, data may be collected from temperature sensors 107, 112, and 322a, . . . , 322n (and the corresponding temperature sensors on each server exhaust); from humidity sensors 355 and 360; and from flow rate meters 245, 325, and 330. Similarly, control signal data may be collected from air conditioning system 335 (e.g., temperature, humidity, and, if equipped, flow rate settings); from flow control valves 305, 310, 345, and 350; and from fans 238, 233. Similarly, data may be collected from the individual servers regarding each server's performance, allowing that performance data to be correlated to the conditions experienced by the server within test room 200. For example, the collected data from temperature sensors 322a . . . 322n from the server inlets and from the temperature sensors at the corresponding server exhausts (not shown) may be collected to show, by their differential, heat dissipating for each server under various supply air 235 temperatures and humidities, under various air inlet flow rates (controlled by, e.g., flow rate valves 305, 310), or from various directions (e.g., from lower inlet 105, from upper air inlet 205, or from a combination of the two), or from combinations of these test room parameters. One of skill will know that a data acquisition system may be used to collect similar measurement and control data from the rack test room embodiments. In FIG. 3, data acquisition system 370 is shown without direct connections to any of the data measuring devices. The connections are not shown for clarity. One of skill will know that data measuring devices may provide data to a data acquisition system through hard wiring, or through wireless arrangements, or through some combination.

Figure 4:
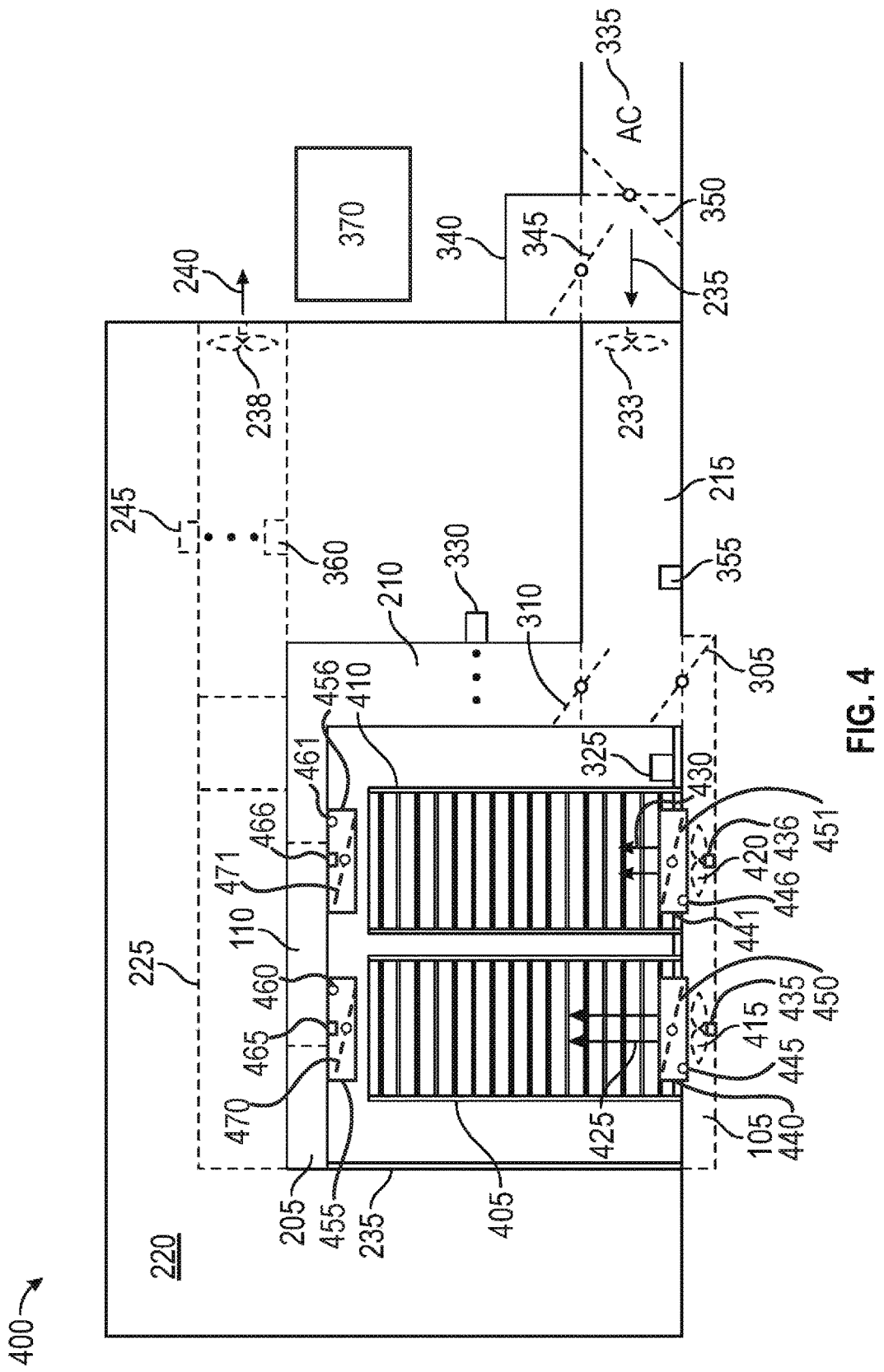
FIG. 4 is a side view drawing illustrating an embodiment of a rack test room.

FIG. 4 is a side view drawing illustrating an embodiment of a rack test room 400. In FIG. 4, rack test room 400 provides the ability to independently control the flow of air directed to individual server racks. In test room 400, a server rack 405 and a server rack 410 have been positioned with the inlets of the servers facing air inlet 105. Air inlet 105 has been provided with a fan 415 and a fan 420. Fans 415, 420 are independently controllable, with fan 415 oriented to direct airflow 425 toward rack 405, and fan 420 oriented to direct airflow 430 toward rack 410. The different relative lengths of the arrows representing airflow 425 and the arrows representing airflow 430 indicate that these airflows may be different. Airflows 425, 430 may be measured by airflow meters 435, 436 positioned to measure each flow, which may provide data to the data acquisitions system 370. In an embodiment, upper inlet 205 is similarly equipped with fans to individually direct air toward racks 405, 410. In an embodiment, in addition to or instead of fans 415, 420, air inlet 105 may be fitted with controllable damper/louver combinations (not shown). In the embodiment, a first damper/louver combination may be controlled to direct air toward rack 405 and the second damper/louver combination may be controlled to direct air toward rack 410. For each damper/louver combination, the damper may be controlled to regulate air flow rate and the louver may be controlled to regulate flow direction. As discussed with reference to FIG. 3, test room 400, the racks, and servers may be fitted with temperature measuring devices and data from the various measuring devices (e.g., temperature, flow rate, and humidity), and data regarding the various control signals (e.g., flow control, fan control, air conditioning control) may be recorded by data acquisition system 370. In an embodiment, additional fans, or additional damper/louver combinations, or both may be added if the ability to test additional server racks using independently controllable airflows is desired. In an embodiment, a rack test chamber 400 for providing a controlled and monitored environment for server racks 405, 410 comprises: first air inlets 440, 441 disposed in a lower area in a first side of chamber 400, each first air inlet 440, 441 corresponding to a position of one of server racks 405, 410 and having a corresponding temperature-measuring device 445, 446 for measuring air temperature, a flow-rate measuring device 435, 436 for measuring air flow rate and a controllable air valve 450, 451 for controlling air flow; second air inlets 455, 456 disposed in an upper area in the first side of chamber 400, each second air inlet 455, 456 corresponding to a position of one server racks 405, 410 and having a corresponding temperature-measuring device 460, 461 for measuring air temperature, a flow-rate measuring device 465, 466 for measuring air flow rate and a controllable air valve 470, 471 for controlling air flow; an air exhaust 110 disposed in a second side of the chamber having temperature-measuring device 112 (FIG. 1) for measuring air temperature in the air exhaust; and humidity measuring device 355 for measuring humidity in any of the first air inlets or second air inlets.

In an embodiment, test room 100, 200, and 400 may be set up to simulate the environment a rack would experience in a data center. In the embodiment, the simulated data center environment may be used to determine how the rack, or the servers within the rack, would perform if they were placed in the environment of the data center. For the embodiment, environmental data from the data center is acquired. Such environmental data may include supply air temperature and humidity, inlet air flow rates, and air inlet locations in relation to the rack. The environmental data may also include the inlet air temperatures for individual servers within the rack. A test room, e.g., test room 200, may then be controlled to simulate the environment of the data center. Such an arrangement may also be used to validate a data center design or improve an existing data center environment by testing the performance of a known-quantity server rack in the proposed data center design or existing environment.

Figure 5:
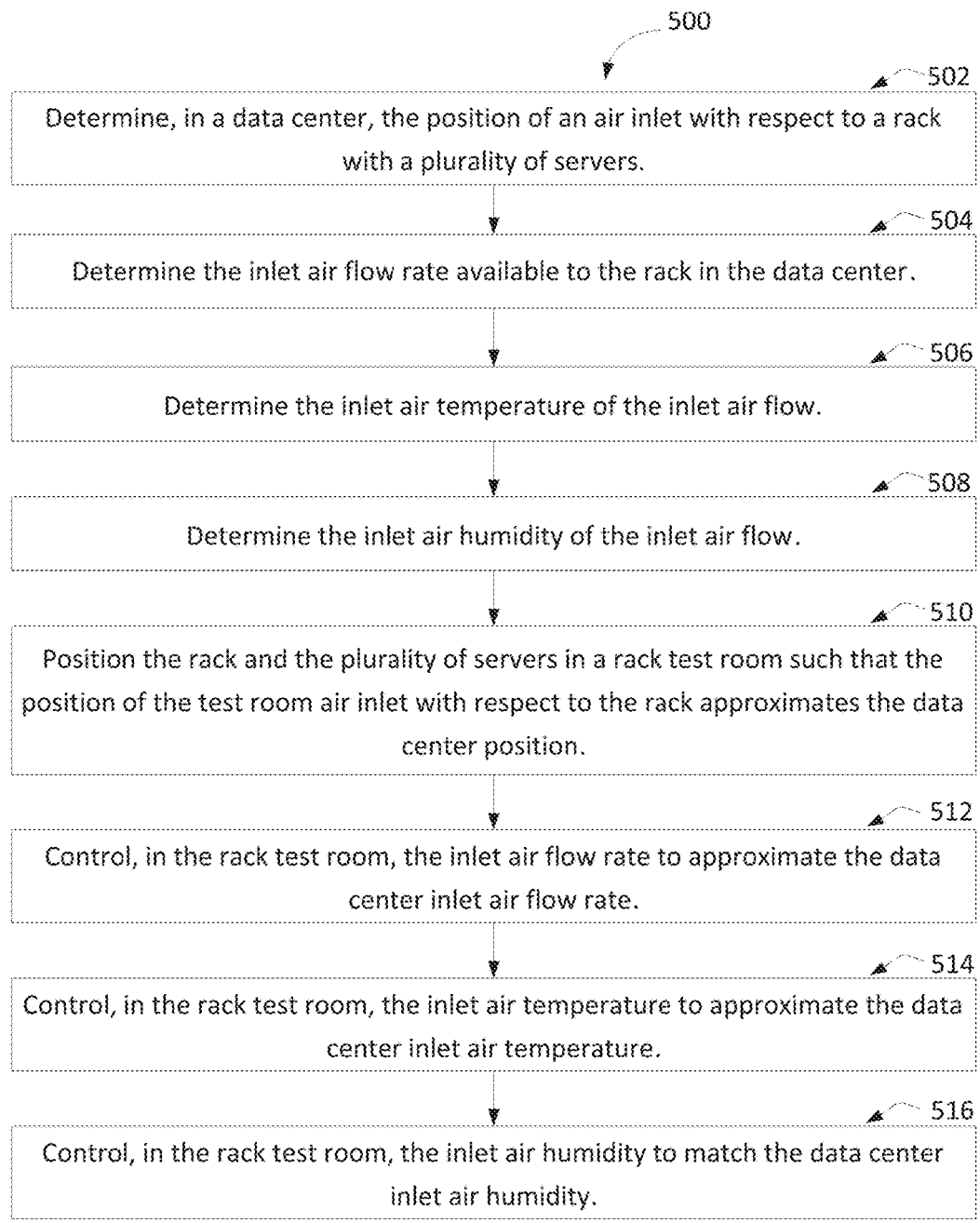
FIG. 5 is an embodiment of a method for using a rack test room.

FIG. 5 is an embodiment of a method 500 for using a rack test room to simulate the environment of a rack in a data center, where the rack may be filled with servers. In method 500, steps 502-508 are performed in the data center and steps 510-516 are performed in an embodiment of a rack test room. In step 502, the position of the data center air inlet with respect to the rack is determined. In step 504, the inlet air flow rate that the rack would experience in the data center is determined. In step 506, the temperature of that airflow is determined. In step 508, the humidity of the airflow is determined. It should be noted that steps are optional, depending on what parameters of the data center environment are to be evaluated. In step 510, the rack with installed servers is positioned in the rack test room such that the air inlet is in substantially the same relative location with respect to the rack as it was in the data center. In step 512, the test room air flow rate is controlled or set to substantially match the air flow rate in the data center. In step 514, the test room inlet air temperature is controlled or set to substantially match the inlet air temperature of the data center. And in step 516, the test room inlet air humidity is controlled or set to substantially match the inlet air humidity of the data center. Regarding the data center environment, the method may determine that a particular data center parameter is found to vary within a range, rather than remain a single value. If so, the corresponding control steps may be modified to control to the range rather than a value. Additionally, such ranges or values may be determined to vary with time. If so, the test room may be controlled such that the appropriate parameter varies with time. That is, the test room environment may be made to vary to simulate variation in the data center environment.

After using method 500 to simulate a data center, the testing of a server rack, e.g., rack 115 in an embodiment of a test room, e.g., test room 200, may indicate that modifications may improve the function of servers in the simulated environment. Those modifications may include modifications to the rack itself or modifications to the rack/server geometry such as spacing between servers. The testing may also indicate that modifications to the data center design or environment itself may improve the function of servers. Those modifications may include changes to the supply air temperature, humidity, flow rate, or inlet direction (e.g., upper or lower).

In other words, in an embodiment, method 500 may be used to evalutate changes to the design of the rack and server in a simulated version of a particular data center environment. Such testing would allow the data center to operate normally. Conversely, the rack and server design may remain fixed, and the parameters of the test room modified to see if they result in an improvement in rack and server performance. Again, this would allow the data center to operate normally. If an improvement is noted, corresponding modifications might be made to the data center environment to enhance the performance of the servers. Thus, changes to a data center environment, or to a rack or servers, may be evaluated without potentially compromising the performance of the data center.

EXPERIMENTAL RESULTS

Figure 6:
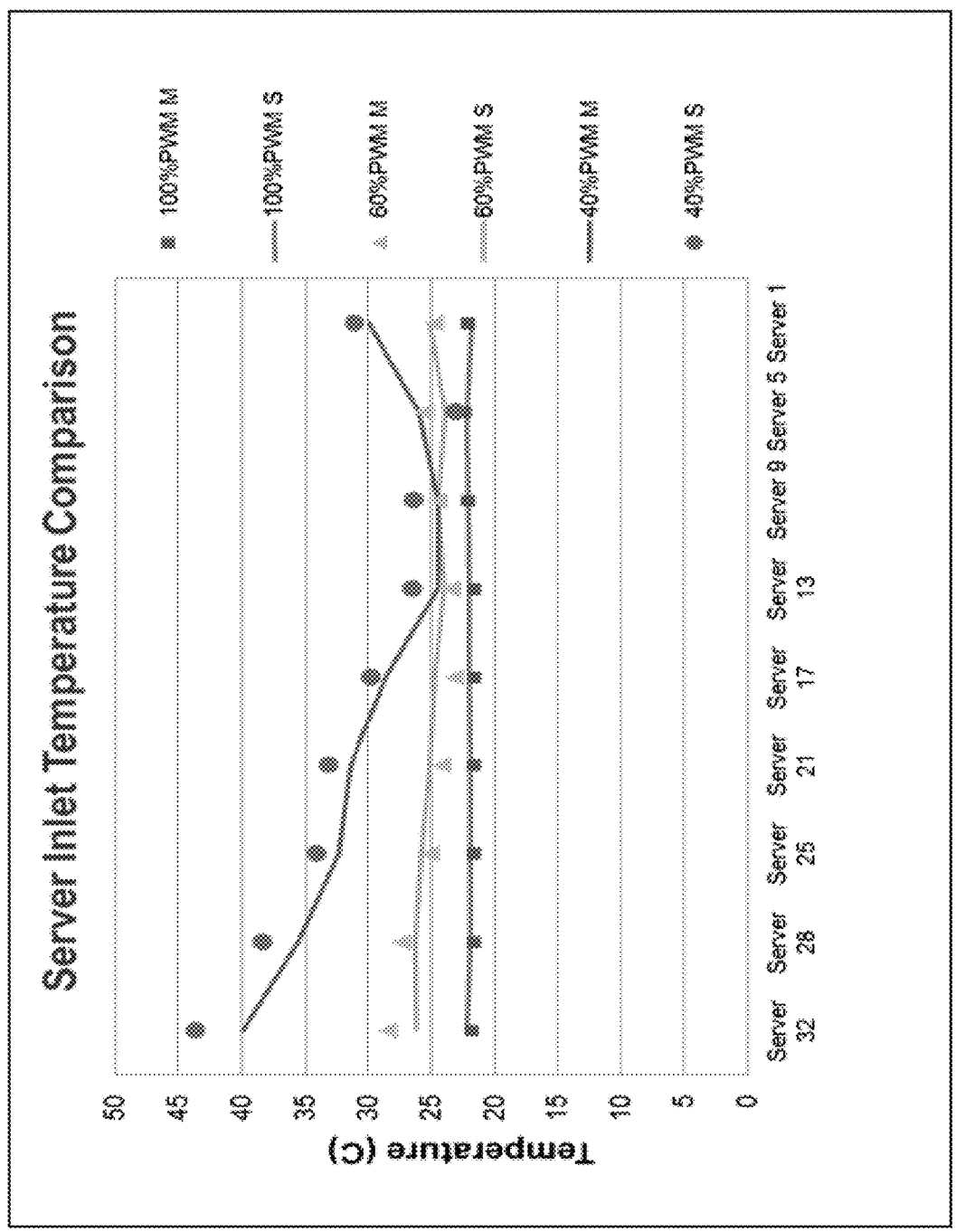
FIG. 6 is a graph illustrating results from testing an embodiment.

FIG. 6 is a graph illustrating results from testing an embodiment. The testing that produced the data in FIG. 6 was designed to verify the functioning of an embodiment of a rack test room. For the testing, a rack with servers 1 through 32 (numbered from lowest to highest in the rack) was operated in a prototype of test room 200. During the testing, the air flow through air inlet 105 was varied to evaluate the impact on the inlet air temperature at some of servers 1 through 32. In the test, the inlet flow rate was changed by varying the duty cycle (i.e., PWM or pulse width modulation) of the power supplied to fan 233. Temperature data was acquired using thermocouples at the inlets of servers 1, 5, 9, 13, 17, 21, 25, 28, and 32. For the test, lower PWM values were interpreted to mean that the inlet air flow rate was correspondingly lower.

In FIG. 6, data points labeled with "M" are measured, actual data points and points labeled "S" are simulated. As can be seen, the measured data points compare favorably with the simulated data points. The resulting data show that at the slowest fan speeds, i.e., the 40% and 60% PWM values, the air temperature at higher server locations was observed to increase over the temperature of the lower servers. The increase was noticeable with the 60% PWM value and was more significant with the 40% PWM value. It was concluded that the fan speed at the lower PWM values allowed air from the hot aisle to recirculate back into the cold aisle. Since the difference in recirculation allowed was first noticeable at 60% PWM, it was concluded that the fan speed could be decreased from 100% PWM to somewhere near 60% PWM without significantly changing the performance of the servers. Such a decrease would save power and related costs. Thus, the testing showed that a benefit of using an embodiment to test a server rack may be a data center cost reduction.

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. For example, one skilled in the art will recognize that these embodiments can be practiced without one or more of the specific details, or with other components, systems, etc. And, in other instances, there may be structures or operations not shown, or not described in detail, to avoid obscuring aspects of the described embodiments. Therefore, the scope of the appended claims should be accorded the broadest interpretation so as to encompass all such modifications and similar arrangements.

What is claimed is:

1. A rack test chamber for providing a controlled and monitored environment for one or more server racks, the rack test chamber comprising:
   a first air inlet disposed in a lower area in a first side of the chamber having a first temperature-measuring device for measuring air temperature in the first air inlet and a first flow-rate measuring device for measuring air flow rate in the first air inlet, the air flow rate in the first air inlet being controlled by a first air valve;
   a second air inlet disposed in an upper area in the first side of the chamber having a second temperature-measuring device for measuring air temperature in the second air inlet and a second flow-rate measuring device for measuring air flow rate in the second air inlet, the air flow rate in the second air inlet being controlled by a second air valve;
   an air exhaust disposed in a second side of the chamber having a third temperature-measuring device for measuring air temperature in the air exhaust; and
   a humidity measuring device for measuring air humidity in the first or second air inlet.

2. The rack test chamber of claim 1 further comprising a data acquisition system, the data acquisition system configured to receive:
   flow-rate data from the first and second flow-rate measuring devices;
   temperature data from the first, second, and third temperature measuring devices;
   humidity data from the humidity measuring device;
   server air inlet temperature data from each of a plurality of servers; and
   server air exhaust temperature data from each of the plurality of servers.

3. The rack test chamber of claim 2, the data acquisition system configured to receive:
   first control signal data from the first controllable air valve;
   second control signal data from the second controllable air valve;
   temperature control signal data from an air-conditioning system;
   humidity control signal data from the air-conditioning system; and supply fan or blower control signal data from the air-conditioning system.

4. The rack test chamber of claim 3, further comprising:
a third controllable air valve for controlling a third air flow from the air exhaust; and
a third flow-rate measuring device disposed to measure an air exhaust flow rate, the data acquisition system further configured to receive flow-rate data from the third flow-rate measuring device and third control signal data from the third controllable air valve.

5. The rack test chamber of claim 4, further comprising an exhaust fan or blower, the data acquisition system configured to receive exhaust fan or blower control signal data.

6. The rack test chamber of claim 1, further comprising a duct directing air from the air exhaust to an air conditioning system.

7. The rack test chamber of claim 1, further comprising a membrane, the membrane dimensioned to accommodate one or more server racks and dimensioned to inhibit air flowing from the first or second air inlet to the first air exhaust from flowing past the one or more server racks.

8. A rack test chamber for providing a controlled and monitored environment for a plurality of server racks, the rack test chamber comprising:
a plurality of first air inlets disposed in a lower area in a first side of the chamber, each of the plurality of first air inlets corresponding to a position of one of a plurality of server racks and having a corresponding first temperature-measuring device for measuring air temperature, a first flow-rate measuring device for measuring air flow rate and a first controllable air valve for controlling air flow;
a plurality of second air inlets disposed in an upper area in the first side of the chamber, each of the plurality of second air inlets corresponding to a position of one of the plurality of server racks and having a second corresponding temperature-measuring device for measuring air temperature, a second flow-rate measuring device for measuring air flow rate and a second controllable air valve for controlling air flow;
an air exhaust disposed in a second side of the chamber and having a third temperature-measuring device for measuring air temperature in the air exhaust; and
a humidity measuring device for measuring humidity in any of the plurality of first air inlets or second air inlets.

9. The rack test chamber of claim 8 further comprising a data acquisition system, the data acquisition system configured to receive:
flow-rate data from each of the plurality of first and plurality of second flow-rate measuring devices;
temperature data from each of the first, second, and third temperature measuring devices;
humidity data from the humidity measuring device;
server air inlet temperature data from each of a plurality of servers; and
server air exhaust temperature data from each of the plurality of servers.

10. The rack test chamber of claim 9, the data acquisition system configured to receive:
first control signal data from each of the plurality of first controllable air valves;
second control signal data from each of the plurality of second controllable air valves;
temperature control signal data from an air-conditioning system;
humidity control signal data from the air-conditioning system; and
supply fan or blower control signal data from the air-conditioning system.

11. The rack test chamber of claim 10, further comprising:
a third controllable air valve for controlling a third air flow from the air exhaust; and
a third flow-rate measuring device disposed to measure an air exhaust flow rate, the data acquisition system further configured to receive flow-rate data from the third flow-rate measuring device and third control signal data from the third controllable air valve.

12. The rack test chamber of claim 11, further comprising an exhaust fan or blower, the data acquisition system configured to receive exhaust fan or blower control signal data.

13. The rack test chamber of claim 8, further comprising a duct directing air from the air exhaust to an air conditioning system.

14. The rack test chamber of claim 8, further comprising a membrane, the membrane dimensioned to accommodate one or more server racks and dimensioned to inhibit air flowing from the first or second air inlet to the first air exhaust from flowing past the one or more server racks.

\* \* \* \* \*